(12) United States Patent
Schuessler

(10) Patent No.: US 10,524,897 B2
(45) Date of Patent: ***Jan. 7, 2020

(54) LIGHTER WEIGHT IMPLANT

(71) Applicant: Allergan, Inc., Irvine, CA (US)

(72) Inventor: David Schuessler, Santa Ana, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/040,020

(22) Filed: Jul. 19, 2018

(65) Prior Publication Data

US 2019/0015196 A1 Jan. 17, 2019

Related U.S. Application Data

(63) Continuation of application No. 15/344,262, filed on Nov. 4, 2016, now Pat. No. 10,052,192, which is a continuation of application No. 14/695,285, filed on Apr. 24, 2015, now Pat. No. 9,486,309.

(60) Provisional application No. 61/984,660, filed on Apr. 25, 2014.

(51) Int. Cl.
*A61F 2/12* (2006.01)

(52) U.S. Cl.
CPC ........ *A61F 2/12* (2013.01); *A61F 2230/0069* (2013.01); *A61F 2250/0003* (2013.01)

(58) Field of Classification Search
CPC ........................................................ A61F 2/12
USPC ......................................................... 623/7–8
See application file for complete search history.

(56) References Cited

U.S. PATENT DOCUMENTS

| 4,380,569 | A |   | 4/1983  | Shaw |
|-----------|---|---|---------|------|
| 4,650,487 | A |   | 3/1987  | Chaglassian |
| 4,773,909 | A |   | 9/1988  | Chaglassian |
| 5,171,269 | A |   | 12/1992 | Bark |
| 5,437,824 | A |   | 8/1995  | Carlisle et al. |
| 5,534,023 | A | * | 7/1996  | Henley ............ A61F 2/12 623/7 |
| 5,658,330 | A |   | 8/1997  | Carlisle |
| 5,824,081 | A |   | 10/1998 | Knapp |
| 5,843,189 | A | * | 12/1998 | Perouse ............ A61F 2/12 623/8 |
| 5,902,335 | A |   | 5/1999  | Snyder, Jr. |
| 5,961,552 | A |   | 10/1999 | Iversen et al. |
| 5,964,803 | A | * | 10/1999 | Iversen ............ A61F 2/12 623/8 |
| 6,066,220 | A |   | 5/2000  | Schneider-Nieskens |
| 6,099,565 | A |   | 8/2000  | Sakura |

(Continued)

FOREIGN PATENT DOCUMENTS

EP   2550942 A1   1/2013
EP   1877002 B1   3/2013

(Continued)

OTHER PUBLICATIONS

G&G Biotechnology Ltd., B-Lite Lightweight Breast Implants, Product Brochure, Jun. 2011.

*Primary Examiner* — Suzette J Gherbi
(74) *Attorney, Agent, or Firm* — Nathan S. Smith; Morgan, Lewis & Bockius LLP

(57) ABSTRACT

A breast implant is provided which includes a filling, or core having a lower overall density relative to silicone gel-filled or saline-filled implant. The core may be a composite including flexible, bodies, for example, air-containing, or gas-containing, bodies, and a gel medium between or around the bodies.

16 Claims, 6 Drawing Sheets

(56) References Cited

U.S. PATENT DOCUMENTS

| | | | |
|---|---|---|---|
| 6,544,287 B1 | 4/2003 | Johnson et al. | |
| 6,644,246 B1* | 11/2003 | Cwik | B01B 1/005 |
| | | | 122/4 D |
| 6,811,570 B1 | 11/2004 | Gehl | |
| 7,789,911 B2 | 9/2010 | Hamilton | |
| 7,875,074 B2 | 1/2011 | Chen et al. | |
| 7,988,731 B2 | 8/2011 | Govrin-Yehudian et al. | |
| 7,988,986 B2 | 8/2011 | Beisang et al. | |
| 8,197,542 B2 | 6/2012 | Becker | |
| 9,486,309 B2* | 11/2016 | Schuessler | A61F 2/12 |
| 9,539,086 B2* | 1/2017 | Schuessler | A61F 2/12 |
| 9,808,338 B2* | 11/2017 | Schuessler | A61F 2/12 |
| 10,052,192 B2* | 8/2018 | Schuessler | A61F 2/12 |
| 2004/0176493 A1 | 9/2004 | Ferguson | |
| 2005/0049701 A1 | 3/2005 | Brennan | |
| 2005/0055093 A1 | 3/2005 | Brennan | |
| 2005/0080338 A1* | 4/2005 | Sirimanne | A61K 49/006 |
| | | | 600/431 |
| 2006/0246121 A1 | 11/2006 | Ma et al. | |
| 2007/0050027 A1 | 3/2007 | McGhan et al. | |
| 2007/0293945 A1 | 12/2007 | Snyder | |
| 2009/0299472 A1 | 12/2009 | Huang | |
| 2010/0029802 A1 | 2/2010 | Mehrabi et al. | |
| 2010/0137985 A1* | 6/2010 | Purkait | A61F 2/12 |
| | | | 623/8 |
| 2011/0106249 A1 | 5/2011 | Becker | |
| 2012/0010705 A1 | 1/2012 | Laghi et al. | |
| 2012/0071973 A1 | 3/2012 | Rechenberg | |
| 2012/0123535 A1* | 5/2012 | Alejandro | A61F 2/12 |
| | | | 623/8 |
| 2012/0165934 A1 | 6/2012 | Schuessler | |
| 2012/0197393 A1 | 8/2012 | Yu | |
| 2012/0277860 A1 | 11/2012 | Dvir et al. | |
| 2014/0039618 A1* | 2/2014 | Becker | A61F 2/12 |
| | | | 623/8 |
| 2014/0081076 A1* | 3/2014 | Schutt | A61B 90/02 |
| | | | 600/31 |
| 2014/0135924 A1* | 5/2014 | Renke | A61F 2/12 |
| | | | 623/8 |
| 2014/0222145 A1* | 8/2014 | Kronowitz | A61F 2/12 |
| | | | 623/8 |
| 2015/0245902 A1* | 9/2015 | Becker | A61F 2/12 |
| | | | 623/8 |
| 2015/0327985 A1* | 11/2015 | Hristov | A61F 2/12 |
| | | | 623/8 |
| 2015/0351900 A1* | 12/2015 | Glicksman | A61F 2/12 |
| | | | 623/8 |
| 2015/0374487 A1* | 12/2015 | Greenberg | A61F 2/07 |
| | | | 623/1.13 |

FOREIGN PATENT DOCUMENTS

| | | |
|---|---|---|
| WO | 1998010803 A1 | 3/1998 |
| WO | 2011133943 A1 | 10/2011 |

* cited by examiner

LIGHTER WEIGHT IMPLANT

CROSS-REFERENCE

This application is a continuation of U.S. patent application Ser. No. 15/344,262, filed on Nov. 4, 2016, which is a continuation of Ser. No. 14/695,285, filed on Apr. 24, 2015, now U.S. Pat. No. 9,486,309, which claims priority to, and the benefit of, U.S. Provisional Patent Application Ser. No. 61/984,660, filed on Apr. 25, 2014, the entire disclosure of each of these applications being incorporated herein by this specific reference.

The present invention generally relates to implantable prosthetic devices and specifically relates to implantable prosthetic devices, for example, breast implants, of reduced weight.

Reconstructive and cosmetic surgery using prosthetic implants is a common practice. For example, reconstructive breast surgery is commonly practiced to allow reconstruction of a woman's breast that was affected by procedures such as mastectomy. Cosmetic breast surgery has also become available to amend the appearance of a woman's breast, for example by adding an implant to increase the size of the breast, to correct asymmetries, change shape and fix deformities.

For reconstructive and cosmetic surgery, a breast implant is required to be able to provide a specific three-dimensional shape and maintain that shape for many years, typically for at least ten years, from which the implant is introduced into the breast. The implant is also required to provide the implanted breast with the feel of a natural human breast.

Conventional breast implants typically comprise an outer shell or envelope typically formed from cured silicone elastomer. The shell can be single or multi layered, and can be smooth or textured. The shell, being in the form of an envelope or pocket, encloses or contains a core or filling, usually silicone gel or saline. A saline filling can be contained in the shell before surgery, or may be introduced into the shell during or after surgery. Silicone gel implants typically are implanted in their fully completed form.

A typical conventional breast implant may weigh between 50 to 1000 grams, depending of course on the volume and the type of material from which is it is made. However, commercially available breast implants, whether filled with silicone gel or saline, generally have an overall product specific gravity close to one, similar to the specific weight of the natural breast tissue.

Nevertheless, natural breast tissue is a live tissue undergoing a common natural lifecycle just as any other tissue within the body, while a breast implant is "dead weight" contained by body tissue. Both natural breast tissue and breast implants are subjected to forces of gravity. The most common response of both natural breast tissue and breast implants to gravitational force over time is sagging and pulling of the skin and overlying tissue structures. Unfortunately, the rate of sagging may be enhanced in implanted breasts.

Some breast implant patients may experience other undesirable consequences related to the weight of the implants. Such problems include excess ptosis of the breasts, tissue atrophy, prominence of the implant through breast tissue, back pain, and/or formation of striae on the skin. Reconstructive surgery patients may be especially prone to such problems when much of the natural supporting breast tissue may have been removed as a result of a mastectomy procedure, leaving less tissue to cover and support an underlying implant. For these patients, a lighter weight implant would be especially desirable.

A variety of products and methods have been proposed to produce a lighter weight breast implant. Shaw, U.S. Pat. No. 4,380,569 discloses the use of hollow glass spheres, which are added to a silicone gel fillers to reduce the overall density, and therefore the weight, of a breast implant. Govrin-Yehudian, U.S. Pat. No. 7,988,731 discloses a double lumen-type breast implant having with materials of differing densities. Schuessler, U.S. patent application Ser. No. 13/327,038, describes a flexible, collapsible prosthesis made of a cellular material. U.S. Pat. No. 5,658,330 to Carlisle, et al. describes a molded foam implant.

Various proposals in the art have been directed at reducing the weight of breast implants while maintaining a natural look and feel. However, there is still a great need for an improved, lighter weight breast implant.

SUMMARY

The present invention provides a prosthetic implant, for example, a breast implant which has a reduced weight relative to conventional gel or saline implants, and which also has natural look and feel when implanted.

The implant generally comprises a shell, which may be a conventionally made cured silicone elastomer, and a core, contained within the shell. The core of the present implants has a lower overall density relative to silicone gel or saline. In one aspect, the core comprises a composite material. More specifically, the core may comprise a hollow body or bodies, for example, air-containing, or gas-containing, bodies, and a medium between or around the bodies. The medium may comprise a silicone gel, for example, a fluid silicone gel or a cohesive silicone gel, which surrounds the bodies.

As used within the scope of the present disclosure, the hollow bodies are considered to be bodies having at least one void or cavity enclosed by a solid material. Hollow bodies include bodies having one of multiple cavities, such as micro-cavities, as well as bodies having cavities of tens of millimeters or greater in size. In some embodiments, the bodies, overall, have a specific gravity of less than 1. Preferably, the bodies provide a lightness to the implant relative to an otherwise identical saline or silicone gel-filled implant not comprising or including the one or more hollow bodies.

In one aspect, the hollow bodies are extruded or molded bodies, for example, made of a polymer such as a silicone-based polymer, for example, a medical grade, cured silicone polymer. The bodies are constructed with voids or cavities. The voids or cavities contain a gas, for example, air, or other suitable gas or gaseous medium. The bodies may have very thin walls or small diameters or cross sections, and may generally be flexible, soft and pliable.

In one embodiment, the bodies comprise tubing, for example, silicone tubing. The tubing may have an outer diameter of about 1 mm to about 10 mm, more preferably from about 2 mm to about 5 mm. The tubing is flexible and compressible providing an additional compliance and softness to the device. In some embodiments, the breast implant includes a single continuous length of tubing. In other embodiments, a breast implant includes tubing comprising a plurality of separate lengths of tubing. Each end of the tubing, or segments of the tubing, may be tied off or plugged closed in order to contain the air (or other gaseous) medium within the hollow bore of the tubing, and not allow ingress of the fluid medium portion of the core.

The fluid medium in which the bodies are contained may be air, saline or other aqueous medium, or gel, for example, silicone gel, for example, cohesive silicone gel. The implant could be constructed as a single lumen, or as a double lumen.

The hollow bodies may be in the form of other extruded shapes having voids, for example, closed cells, for containing air or other gas.

In some embodiments, a breast implant is provided comprising a shell, a core or filling enclosed by the shell, and the filling comprising a gel medium and a plurality of gas-containing bodies. The filling has a relatively higher concentration of gas-containing bodies in at least one region of the filling relative to another region of the filling, thereby providing an implant having a variable density. In some embodiments, gas-containing bodies are tubes, and the tubes are more highly concentrated in a posterior portion of the implant than in an anterior portion of the implant.

Each and every feature described herein, and each and every combination of two or more of such features, is included within the scope of the present invention provided that the features included in such a combination are not mutually inconsistent.

BRIEF DESCRIPTION OF THE DRAWINGS

The present invention may be better appreciated, and its aspects, advantages and features better understood, with consideration given to the following Detailed Description and Drawings in which.

DETAILED DESCRIPTION

Figure 1:
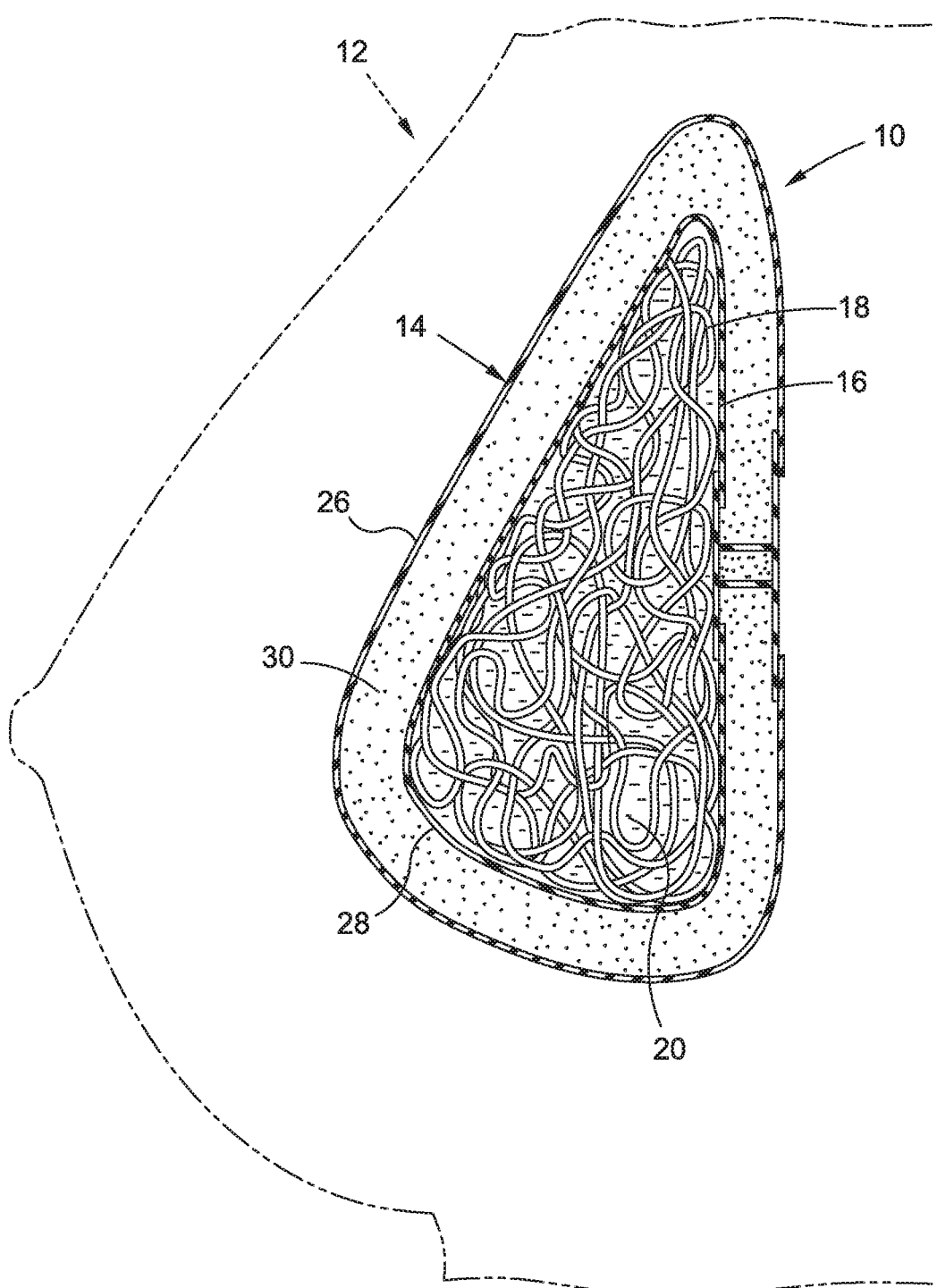
FIG. 1 is a cross-sectional view of an implant in accordance with an embodiment of the invention.

Turning now to FIG. 1, a breast implant 10 in accordance with one embodiment, is shown in simplified form, in a breast 12. The implant 10 generally comprises a shell 14 and a filling 16 enclosed by the shell 14. The filling 16 comprises at least one flexible hollow body 18 and a medium 20 containing the body 18.

Figure 2:
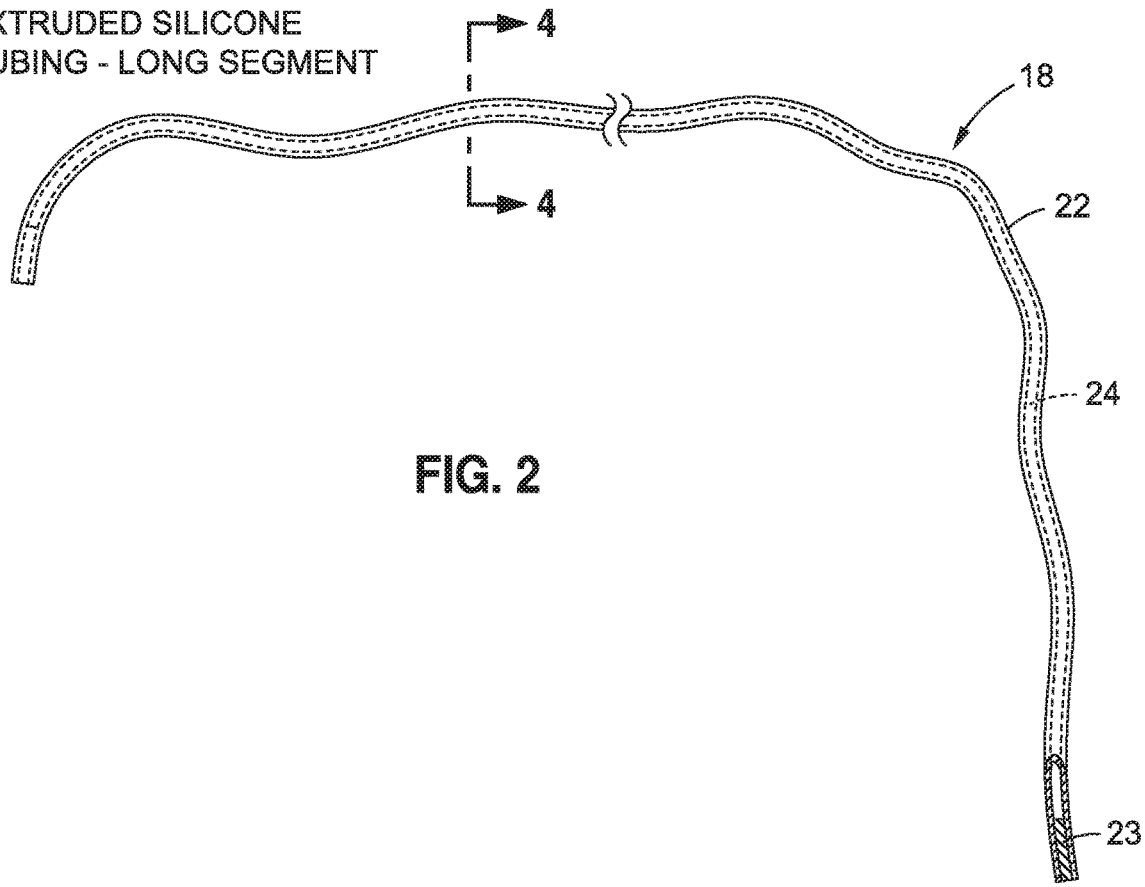
FIG. 2 is a perspective view of a single hollow body component of the implant shown in FIG. 1.

As shown in FIG. 2, the body 18 may comprise an elongated body, for example, in the form of a tube 22. The tube 22 may be sealed for example with appropriate structure 23 in such a manner such the medium 20 (not shown in FIG. 2) does not enter the hollow cavity or bore 24 of the tubing 18.

Turning back to FIG. 1, the medium 20 may be any suitable fluid medium, for example a liquid medium, for example, saline or other suitable biocompatible liquid medium.

In some embodiments, the medium 20 is a gel, for example a silicone gel, for example a fluid silicone gel or, alternatively, a more stable, firm silicone gel, such as a substantially non-flowable silicone gel, also sometimes referred to in the industry as a "form stable gel." Such gels are known in the breast implant art and thus will not be described in greater detail herein.

As shown, the implant 10 could be constructed with multiple lumens, for example, as a double lumen implant. For example, shell 14 may make up an outer lumen 26 that encloses an inner lumen 28, which contains the filling 16. Between the outer lumen 26 and inner lumen 28 may be disposed a silicone gel 30, or other suitable medium such as saline, which at least partially surrounds the inner lumen 28.

Tubing 22 may be made of a soft molded, for example, extruded material, such as a soft silicone or other biocompatible polymeric material.

In some embodiments, tubing 22 has an outer diameter of between about 1 mm and about 10 mm, for example, between about 2 mm and about 5 mm. Tubing may have an outer diameter of, for example, about 1 mm , about 2 mm, about 3 mm, about 4 mm, about 5 mm, about 6 mm, about 7 mm, about 8 mm, about 9 mm, about 10 mm, or greater. Tubing 18 may have a wall thickness of between about 0.5 mm and about 4 mm, for example, about 1 mm, about 1.5 mm, about 2 mm, about 2.5 mm, about 3 mm, about 3.5 mm, about 4 mm, about 4.5 mm, or about 5 mm, or greater. Bore 24 may have a diameter of, for example, about 0.5 mm and about 4 mm, for example, about 1 mm, about 1.5 mm, about 2 mm, about 2.5 mm, about 3 mm, about 3.5 mm, about 4 mm, about 4.5 mm, or about 5 mm, or greater.

In some embodiments filling 16 comprises, or consists essentially of, a single strand of tubing 22.

Figure 3:
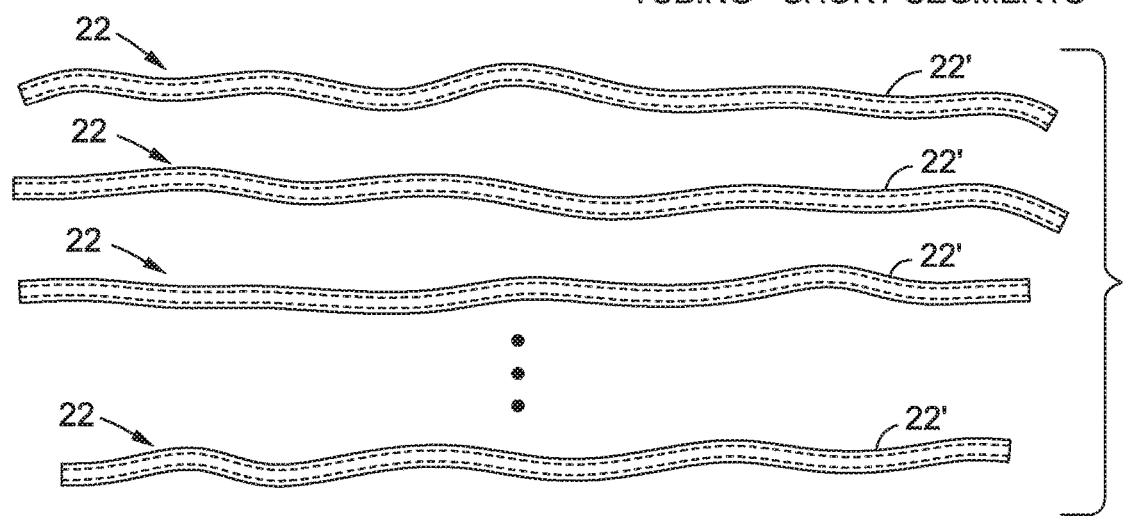
FIG. 3 is a perspective view of a plurality of hollow bodies which may be used as an alternative to the single hollow body component shown in FIG. 2.

In other embodiments, tubing 22 may be in the form of, or comprise, a plurality of separate tubing segments 22', such as shown in FIG. 3. For example, filling 16 may comprise up to about 10, about 20, about 30, about 40, about 50, about 100, or more tubing segments 22'.

Figure 4:
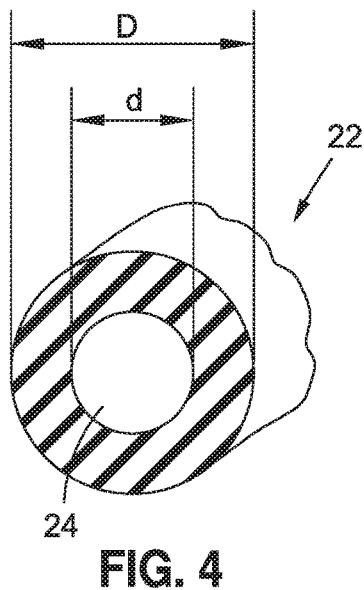
FIG. 4 is a cross sectional view of the hollow body component shown in FIG. 2.
Figure 5:
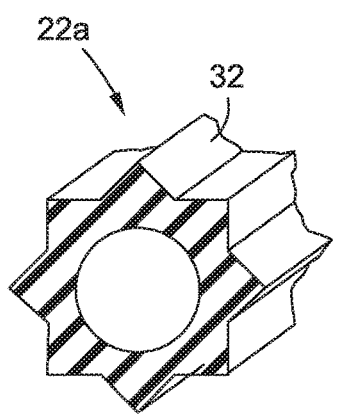
FIGS. 5 and 6 show, respectively, two different alternative cross-sectional shapes for hollow body components such as shown in FIG. 2.
Figure 6:
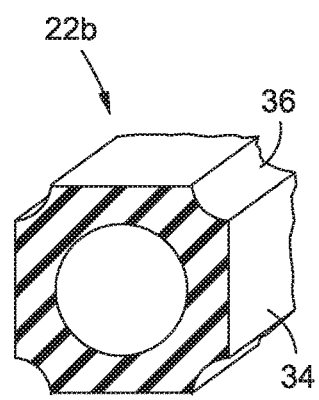

Various exemplary cross sectional shapes of tubing 22 are shown in FIGS. 4-6. FIG. 4 shows cylindrical tubing 22 with outer diameter D and inner diameter d defining bore 24. FIG. 5 shows tubing 22a having a somewhat star shaped cross section defined by a number of ridges, in this embodiment, eight ridges 32. Other cross sections are contemplated, for example, tubing 22b having a rectangular cross section, such as shown in FIG. 6, defined by planar portions 34 and intermediate concave portions 36.

Figure 7:
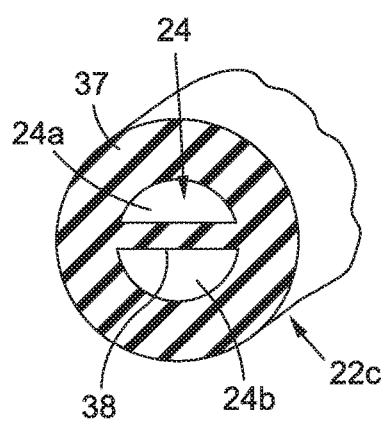
FIGS. 7, 8 and 9 show respectively, cross-sections of three other hollow body components.
Figure 8:
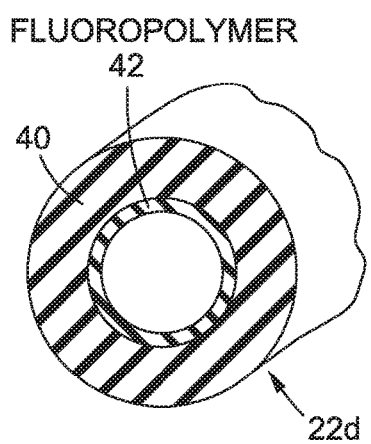
Figure 9:
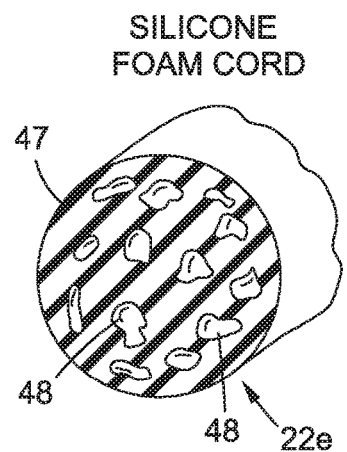

Still other tubing configurations are contemplated, for example, tubing 22c, 22d and 22e shown in FIGS. 7-9, respectively. These configurations are structured to reduce the chance, or to prevent the tubing structure from collapsing.

For example, tubing 22c, shown in FIG. 7, includes wall 37 and divisor portion 38, separating bore 24 into separate bores 24a and 24b. Divisor portion 38 prevents tubing 22c from collapsing under pressure and maintains shape integrity of tubing 22c.

Tubing 22d, shown in FIG. 8, is in the form of a multilayered tubing, for example, a two-layered tubing, including a first material 40, for example, silicone, and a second material 42, for example, a fluoropolymer. Tubing 22d may be in the form of a sealed body containing air or other gaseous component in a cavity defined by tubing material 40. Advantageously, second material 42 is a material that substantially or completely prevents diffusion of air (or other gaseous component) out of the tubing 22d, thereby preventing collapse and maintaining integrity of tubing 22d.

Still further, tubing 22e, shown in FIG. 9, is in the form of a cord 47 having voids 46, instead of the bore 24 of some of the earlier described embodiments. The cord may be an extruded foam material for example, an extruded silicone foam. The foam is preferably a closed-cell foam.

Figure 10:
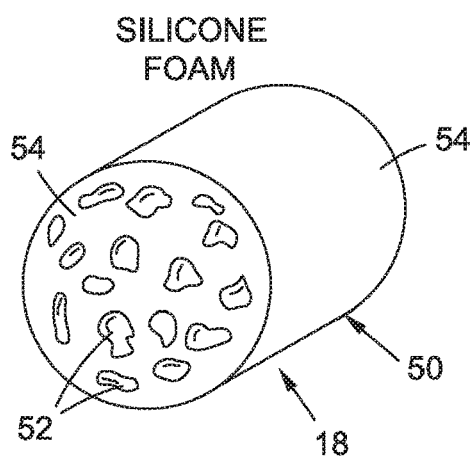
FIG. 10 is a perspective view of yet another hollow body component of an implant of the present invention.
Figure 11:
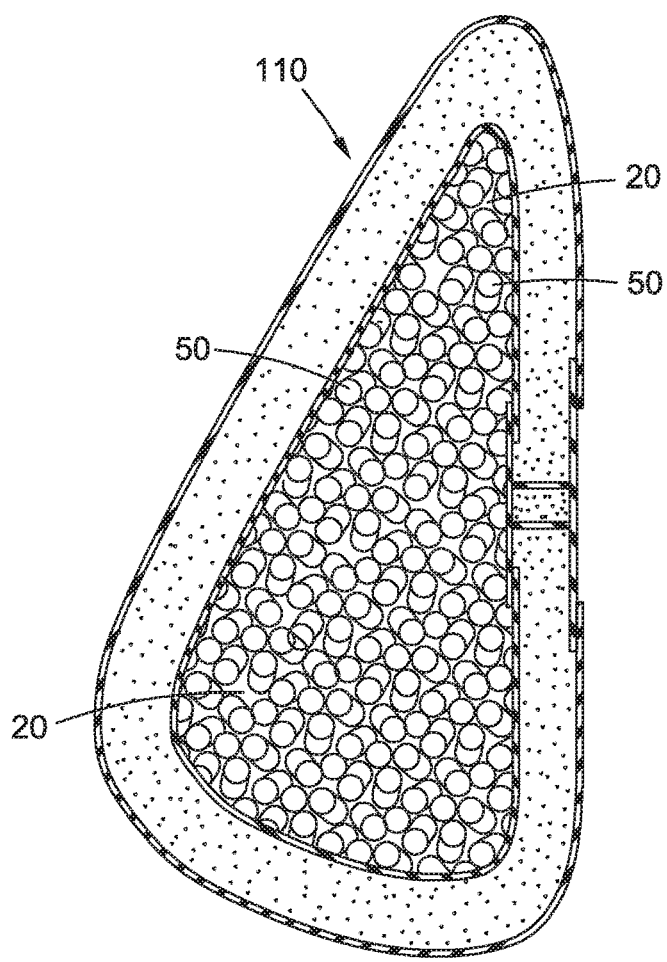
Figure 14:
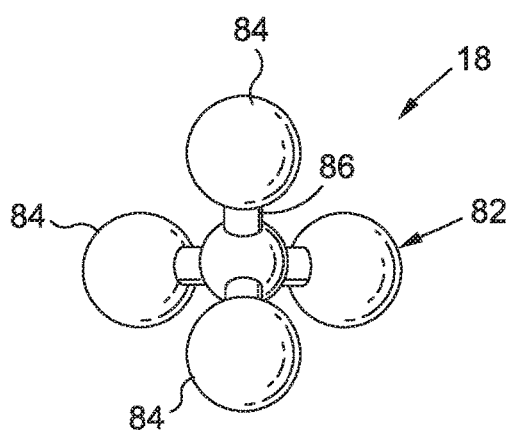
FIG. 14 is a perspective view of yet another hollow body component of an implant of the present invention.

Turning now to FIGS. 10 and 11, a breast implant 110 is shown, which may be substantially the same as implant 10, except that instead of tubing 22, hollow bodies 18 are in the form of members 50, for example, foam-like members 50 having voids 52, preferably closed voids 52 which contain a gas such as air. Members 50 may have any suitable shape, for example, a cylindrical shape such as shown in FIG. 10, and may be made of a foam or sponge-like material 54 that is substantially impermeable by medium 20. For example, in some embodiments, material 54 may be a cured silicone material and medium 20 may be saline. Members 50 may have an outer diameter of about 1 mm to about 10 mm, for example, between about 2 mm to about 5 mm, and a length of about 1 mm to about 10 mm, for example, between about 2 mm to about 5 mm. Members 50 may be present in the implant in a sufficient number, depending on the size or shape of members 50, to provide the desired volume and firmness to implant 110. For example, members 50 may be present in implant 110 in a quantity of about 100, about 1000, about 10,000, or about 100,000 members, for example.

Members and segments 50 may be sized and shaped such that in plurality, they form a pliable, fluid filler material, such as shown in FIG. 11.

Figure 12:
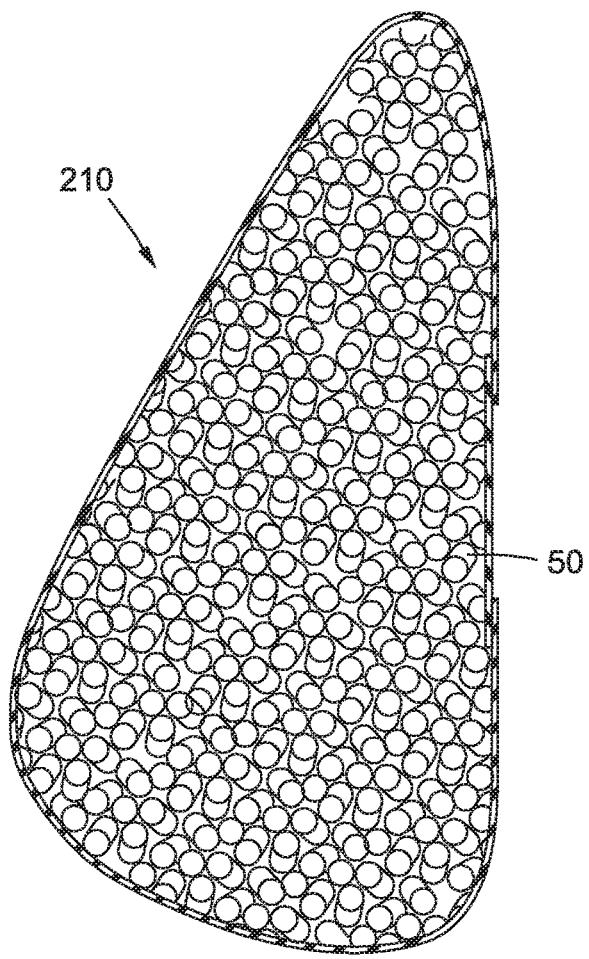
FIGS. 11 and 12 are cross sectional views of additional breast implants in accordance with different embodiments of the invention.

Implant 210, in accordance with another embodiment shown in FIG. 12, may be substantially the same as implant 110, except that it is a single lumen implant rather than a double lumen implant.

Figure 13:
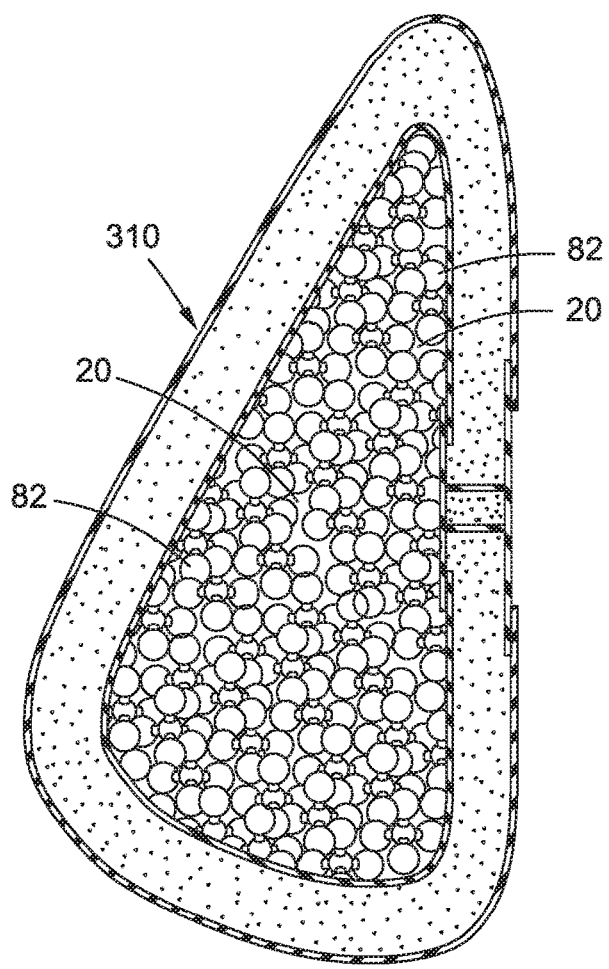
FIG. 13 is a cross-sectional view of an implant in accordance with yet a still further embodiment of the invention.

Turning now to FIG. 13, yet another implant 310 in accordance with the invention is shown.

Figure 15:
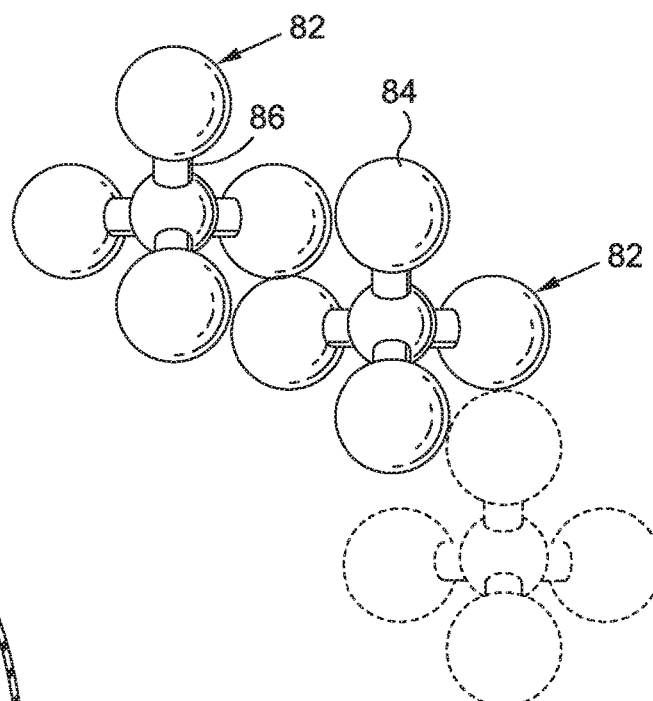
FIG. 15 is an illustration showing arrangement of multiple hollow bodies shown in FIGS. 14.

Implant 310 may be substantially the same as implant 10, 110, or 210 except that the hollow bodies 18 are in the form of members 82 having a somewhat tetrahedral shape which enable them to flow, as a whole, and not become packed together, such as shown in FIG. 15. En masse, the members 82 provide a filling of breast implant 310 having a somewhat fluid movement, providing a desired pliable, natural feel and flexibility to the implant 310.

The members 82 may include enlarged ends 84, for example, spherical ends, that provide for separation between adjacent members 82. Stem regions 86 connecting enlarged ends 84 provide flexibility and interior space for the medium 20 between members 82. In one embodiment, the tetrahedron shaped members 82 have a maximum dimension of between about 10 mm to about 300 mm, for example, between about 50 mm to about 250 mm, for example, between about 100 mm to about 200 mm.

Figure 16:
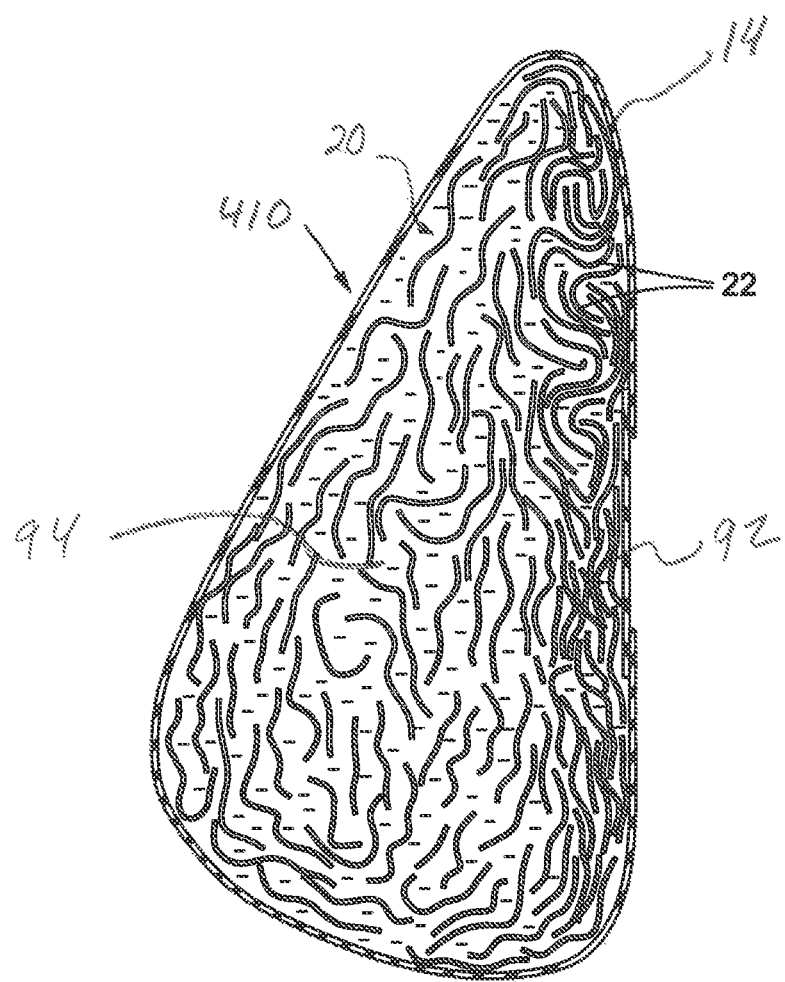
FIG. 16 shows yet another embodiment of the invention.

FIG. 16 shows yet another embodiment of the invention, in the form of a breast implant 410 having regions of different densities formed by different concentrations of members 22 in the medium 20. For example, implant 410 includes shell 14 forming an envelope containing medium 20 for example, a silicone gel filler medium 20, and members 22, (and/or members 22a, 22b, 22c, 22d, or any other members described herein) that are concentrated in certain regions of the implant 410, thus providing a less dense or "lighter" region in the areas having the highest concentration of members 22, and a more dense, or heavier, region in areas having a lower concentration of members 22. This concept provides an implant having a desired variable feel or firmness and/or shape retention, for example, an implant having a softer anterior and a firmer anterior, or vice versa. This may be accomplished, for example, by positioning the implant 410 during curing of the filler medium 20, such that the members 22, which are buoyant in a substantially liquid, uncured silicone gel, will migrate to and become concentrated in a desired area of the implant 410. In the embodiment shown, for example, the members 22 are more concentrated in a posterior region 92 of the implant 410, and relatively less concentrated in an anterior region 94 of the implant 410.

In some embodiments, multiple gel fills and curing process steps can be used to position and concentrate the members 22 where desired in the implant 410, thus creating zones of different densities and feel without the need for a second shell or double lumen design.

While this invention has been described with respect to various specific examples and embodiments, it is to be understood that the invention is not limited thereto and that it can be variously practiced within the scope of the invention.

What is claimed is:

1. A breast implant comprising:
a shell; and
a filling enclosed by the shell;
the filling comprising a gel medium, and a plurality of gas-containing bodies, including a relatively higher concentration of gas-containing bodies in at least one region of the filling relative to another region of the filling, thereby providing an implant having a variable density.

2. The implant of claim 1 wherein the higher concentration is located in a posterior region of the implant.

3. The implant of claim 1 wherein the gas-containing bodies are tubes.

4. The implant of claim 1 wherein the gas-containing bodies are tubes, and the tubes and the tubes are more highly concentrated in a posterior portion of the implant than in an anterior portion of the implant.

5. A breast implant comprising:
a shell; and
a filling enclosed by the shell;
the filling comprising members comprising multiple closed voids defined in the members, and a medium surrounding the members.

6. The implant of claim 5 wherein the multiple closed voids defined in the members contain a gas.

7. The implant of claim 5 wherein the members are a foam material.

8. The implant of claim 5 wherein the members are a silicone foam material.

9. The implant of claim 5 wherein the members are substantially impermeable by the medium.

10. The implant of claim 5 wherein the members are a cured silicone foam and the medium is saline.

11. The implant of claim 5 wherein the medium is a silicone gel.

12. The implant of claim 5 wherein the members are a silicone foam material and the medium is saline.

13. The implant of claim 5 wherein the members have an outer diameter of about 1 mm to about 10 mm.

14. The implant of claim 5 wherein the members have an outer diameter of about 2 mm to about 5 mm.

15. The implant of claim 5 wherein the members have a length of about 1 mm to about 10 mm.

16. The implant of claim 5 wherein the members have a length of about 2 mm to about 5 mm.

\* \* \* \* \*